United States Patent
Docherty

(10) Patent No.: US 7,429,577 B2
(45) Date of Patent: Sep. 30, 2008

(54) AUGMENTATION OF ATYPICAL ANTIPSYCHOTIC AGENT PHARMACOTHERAPY WITH CHROMIUM SUPPLEMENTATION

(75) Inventor: John Docherty, White Plains, NY (US)

(73) Assignee: Comprehensive Neuroscience, Inc., White Plains, NY (US)

( * ) Notice: Subject to any disclaimer, the term of this patent is extended or adjusted under 35 U.S.C. 154(b) by 568 days.

(21) Appl. No.: 10/983,896

(22) Filed: Nov. 9, 2004

(65) Prior Publication Data

US 2005/0096305 A1 May 5, 2005

Related U.S. Application Data

(63) Continuation-in-part of application No. 10/202,389, filed on Jul. 25, 2002, now Pat. No. 6,831,077.

(51) Int. Cl.
*A61K 31/555* (2006.01)
*A61K 31/553* (2006.01)

(52) U.S. Cl. .................... 514/188; 514/211.11
(58) Field of Classification Search ........................ None
See application file for complete search history.

(56) References Cited

U.S. PATENT DOCUMENTS

| 5,087,624 | A | 2/1992 | Boynton et al. |
|---|---|---|---|
| 5,470,846 | A | 11/1995 | Sandyk |
| 5,789,401 | A | 8/1998 | McCarty |
| 5,898,036 | A | 4/1999 | McLeod |
| 6,034,125 | A | 3/2000 | McLeod |
| 6,329,361 | B1 | 12/2001 | McCarty |
| 6,348,455 | B1 | 2/2002 | Yelle |

OTHER PUBLICATIONS

Medline Abstract 2001088284, Bettinger et al., Annals of pharmacotherapy, (Jul.-Aug. 2000) 34 (7-8) 865-7.
Medline Abstract 2002026101, Meyer, Journal of clinical psychopharmacology (Aug. 2001) 21 (4) 369-74.
Boyle, Edwin Jr. et al. "Chromium Depletion in the Pathogenesis of Diabetes and Atherosclerosis" *Southern Medical Journal*, Dec. 1977, 70(12), pp. 1449-1453.
Anderson, Richard A. "Nutritional Factors Influencing the Glucose/Insulin System: Chromium" *Journal of the American College of Nutrition*, 16(5), pp. 404-410, date unavailable.

*Primary Examiner*—Raymond J Henley, III
(74) *Attorney, Agent, or Firm*—Nath Law Group; Joshua B. Goldberg; Ari Zytcer

(57) ABSTRACT

The present invention relates to pharmaceutical compositions comprising an antipsychotic agent in combination with a chromium salt, which are used for minimizing side effects in a patient taking an antipsychotic agent.

17 Claims, No Drawings

AUGMENTATION OF ATYPICAL ANTIPSYCHOTIC AGENT PHARMACOTHERAPY WITH CHROMIUM SUPPLEMENTATION

The present application is a continuation-in-part of U.S. patent application Ser. No. 10/202,389, filed on Jul. 25, 2002 now U.S. Pat. No. 6,831,077, the entire contents of which are hereby incorporated by reference.

FIELD OF THE INVENTION

The present subject matter relates generally to pharmaceutical compositions comprising an antipsychotic agent in combination with a chromium salt, which are used for minimizing side effects in a patient taking an antipsychotic agent. The present subject matter also relates to a treatment for psychotic disorders generally, and in particular to a method of improving the effectiveness of an antipsychotic agent by administering a chromium salt to a patient concurrently with the administration of the antipsychotic agent.

BACKGROUND OF THE INVENTION

Those having ordinary skill in the art will appreciate that psychotic disorders are difficult mental disorders to treat. Patients having such a disorder are often reluctant to seek the medical attention necessary to diagnose the disorder. Such reluctance is often related to the patient's fear of the stigma associated with seeking psychiatric help or to the patient's feelings of worthlessness associated with depression. Moreover, once patients seek competent psychiatric help, it is difficult to successfully treat the disorder through psychoanalytic approaches alone.

Presently, several pharmaceutical agents have been developed which aid in the treatment of psychotic disorders. Clinical experience and published studies indicate the effectiveness of olanzapine as one such agent effective in the treatment of psychotic disorders.

However, the use of these pharmaceutical agents, such as olanzapine, produces numerous side effects in patients. One such common side effect is significant weight gain.

Although not all patients experience this weight gain side effect, in those that do, the weight gain can be considerable, as much as 40-50 pounds. This side effect presents a number of patient issues, both medical and psychological, for the treating physician to consider. Such a marked weight gain can place a significant burden on the heart and circulatory system of the patient. In addition, such weight gain can hurt self-image and adversely impact the depressed state. Additionally, and perhaps most importantly, such side effects can reduce treatment adherence to the therapy regimen, thereby resulting in ineffective treatment for the primary disorder. Finally, significant weight gain increases the risk for diabetes mellitus, hypertriglyceridemia, and long-term cardiovascular risk. Accordingly, the incidence of non-insulin dependent diabetes mellitus (NIDDM) and hyperglycemia is higher in patients suffering from psychotic disorders, such as schizophrenic patients, than in the general population.

It has been suggested that the antipsychotic agents themselves, and olanzapine in particular, are part of the problem as these agents not only increase adiposity, which in itself can decrease insulin sensitivity, but also can impact glucose regulation independently of increases in adiposity. In fact, treatment of non-diabetic patients suffering from schizophrenia with olanzapine and other antipsychotic agents has been associated with negative effects on glucose regulation, which can vary in severity independent of adiposity. For example, olanzapine treatment has been associated with elevated levels of insulin, leptin, and blood lipids, as well as insulin resistance. As such, it is recognized in the art that clinicians should monitor blood glucose concentrations periodically in patients taking olanzapine, especially in those patients with risk factors for diabetes mellitus.

Identification of a means to counteract these side effects partially or completely is, therefore, important. There is at present no way to prevent or treat obesity associated with the use of these antipsychotic agents, except through behavioral changes such as increased physical activity or decreased caloric intake. Accordingly, there remains a need for a method of administering an antipsychotic agent to treat a patient suffering from a psychotic disorder without causing side effects such as weight gain and diabetes mellitus in the patient.

Chromium, in its pharmaceutically acceptable trivalent form, has been used in the treatment of overeating as it is documented to control appetite. Trivalent chromium is commercially available as chromium picolinate. As such, toxicity concerns relating to pharmaceutically acceptable forms of chromium have been demonstrated to be quite low.

Chromium has also long been recognized as being nutritionally essential and in particular it is widely considered necessary for optimum insulin activity (see *Present Knowledge in Nutrition*, The Nutrition Foundation, Washington D.C., 1984, p. 571; Boyle et al., *Southern Med. J.*, 70:1449-1453, 1977, the contents of which are hereby incorporated by reference in their entirety). Chromium improves the glucose/insulin system in subjects with hypoglycemia, hyperglycemia, diabetes, and hyperlipidemia by affecting all key parameters: insulin binding, insulin receptor number, insulin internalization, beta cell sensitivity, and insulin receptor enzymes (see Anderson R A, "Nutritional factors influencing the glucose/insulin system: chromium", *J. Am. Coll. Nutr.*, 16(5): 404-10, October 1997, the contents of which is hereby incorporated by reference in its entirety).

Most of the several studies involving chromium supplementation of subjects with NIDDM and/or lipidemia were performed with chromium picolinate and have reported beneficial effects of chromium supplementation on the glucose/insulin system. Chromium picolinate was shown to be effective on glycemic and lipemic parameters both in healthy volunteers given 200 μg chromium picolinate per day (fasting blood glucose decreased by 24%, glycosylated hemoglobin decreased by 19%, total cholesterol decreased by 13%, and LDL cholesterol decreased by 11%) and in obese Caucasian patients with type-II diabetes receiving sulphonylurea and metformin (lowering fasting insulin levels without impairing glucose control).

In addition to its effects on glycemia, chromium has been implicated as a cofactor in the maintenance of normal lipid metabolism. Further, the bioavailable conjugate chromium picolinate has been shown to be efficacious in lowering blood lipids in humans, in particular in subjects whose plasma cholesterol levels are above the 200 μg/ml level. Additionally, low chromium levels have been shown to increase the risk of coronary heart disease in overweight men.

A method of using chromium to treat neurological and mental disorders was described in Sandyk U.S. Pat. No. 5,470,846. However, the method of this reference includes the application to the brain of a patient of a sufficient amount of an AC pulsed magnetic field of proper intensity and frequency to treat the disorder. In conjunction with the application of the AC pulsed magnetic field, a stimulant to facilitate the transport of tryptophan into the brain is administered.

Chromium, preferably in the form of chromium picolinate, is described as the stimulant. However, when the disclosure of this application of chromium is taken as a whole, the deficiencies become apparent. First of all, the application of the AC pulsed magnetic field is required in the method. Additionally, patients, particularly in the case of psychotic disorders, are known to be resistant to accepting such complex treatments.

Another method of using chromium to reduce hyperglycemia and stabilize levels of serum glucose was described in U.S. Pat. No. 5,789,401. However, the method of this reference includes the co-administration of biotin with chromium tripicolinate to reduce the hyperglycemia.

Yet another method of using chromium to reduce hyperglycemia and stabilize levels of serum glucose was described in U.S. Pat. No. 6,329,361. However, the method of this reference indicates that chromium tripicolinate should be used alone to reduce the hyperglycemia.

U.S. Pat. No. 5,898,036 discloses the ability of chromium to improve the effectiveness of an antidepressant composition. In particular, this patent relates to the ability of chromium to improve the effectiveness of selective serotonin reuptake inhibitors. However, this reference does not in any way indicate that chromium is useful in conjunction with an antipsychotic agent.

Therefore, there is a need in the art for an effective, pharmacologically-based treatment for psychotic disorders that augments the action and reduces the side effects of known compositions, such as antipsychotic agents, used in the treatment of these disorders. Such a treatment is lacking in the prior art.

SUMMARY OF THE INVENTION

In one aspect, the present inventive subject matter relates to a pharmaceutical composition comprising a therapeutically effective amount of an antipsychotic agent in combination with a chromium salt; and a pharmaceutically acceptable carrier.

In another embodiment, the present inventive subject matter additionally relates to a method for minimizing side effects in a patient taking an antipsychotic agent, comprising administering a therapeutically effective amount of said antipsychotic agent in combination with a chromium salt to said patient, wherein said side effects are caused by taking said antipsychotic agent.

In yet another embodiment, the present inventive subject matter relates to a method for reducing weight gain in a patient taking an antipsychotic agent, comprising administering a therapeutically effective amount of said antipsychotic agent in combination with chromium picolinate to said patient, wherein said weight gain is caused by taking said antipsychotic agent.

In still another embodiment, the present inventive subject matter relates to a method for reducing incidence of hyperglycemia in a patient taking an antipsychotic agent, comprising administering a therapeutically effective amount of said antipsychotic agent in combination with chromium picolinate to said patient, wherein said hyperglycemia is caused by taking said antipsychotic agent.

In another preferred embodiment, the present inventive subject matter relates to a method for treating a patient suffering from a psychotic disorder, comprising administering a therapeutically effective amount of an antipsychotic agent in combination with a chromium salt to said patient.

DETAILED DESCRIPTION OF THE INVENTION

As used herein, the terms "pharmaceutically acceptable salts" or "a pharmaceutically acceptable salt thereof" refer to salts prepared from pharmaceutically acceptable non-toxic acids. Such salts may be prepared from pharmaceutically acceptable non-toxic acids including inorganic and organic acids. Suitable pharmaceutically acceptable acid addition salts for the compound of the present invention include acetic, adipic, alginic, p-aminobenzoic, ascorbic, aspartic, benzenesulfamic, benzenesulfonic (besylate), benzoic, bismethylenesalicylic, bisulfuric, bitartaric, boric, butyric, camphoric, camphorsulfonic, cinnamic, citraconic, citric, cyclohexylsulfamic, cyclopentane-propionic, digluconic, dodecylsulfuric, ethanedisulfonic, ethenesulfonic, formic, fumaric, gentisinic, glucaronic, gluconic, glutamic, glycolic, glycerophosphoric, 8-halotheophyllines, hemisulfuric, heptanoic, hexanoic, hydrobromic, hydrochloric, hydroiodic, isethionic, itaconic, lactobionic, lactic, lauric, maleic, malic, malonic, mandelic, methanesulfonic (mesylate), mucic, 2-naphthalenesulfonic, nicotinic, nitric, oleic, oxalic, palmitic, paminobenzoic, pamoic, pantothenic, pectinic, perchloric, phosphoric, picric, pivalic, propionic, pyruvic, saccharic, salicylic, stearic, succinic, sulfamic, sulfuric, tartaric, theophylline acetic acids, thiocyanatic, p-toluenesulfonic, undecanoic, valeric, and the like.

The term "pharmaceutically-acceptable carrier" as used herein means one or more compatible solid or liquid filler, diluents, or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with each other in a manner such that there is no interaction which would substantially impair the desired pharmaceutical efficacy. Examples of such carriers include gels, liquid suspensions, emulsions, creams, ointments, powders, solutions, and lotions.

The term "psychotic disorder" or "psychotic condition" as used herein means pathologic psychological conditions which are psychoses or may be associated with psychotic features. Such conditions include, but are not limited to, the psychotic disorders which have been characterized in the DSM-IV-R, Diagnostic and Statistical Manual of Mental Disorders Revised, 4th Ed. (1994), the entire contents of which are hereby incorporated by reference, including schizophrenia and acute mania. The DSM-IV-R was prepared by the Task Force on Nomenclature and Statistics of the American Association, and provides clear descriptions of diagnostic categories. The skilled artisan will recognize that there are alternative nomenclatures, nosologies, and classification systems for pathologic psychological conditions and that these systems evolve with medical scientific progress.

The term "anxiety disorder" as used herein includes, but is not limited to, obsessive-compulsive disorder, psychoactive substance anxiety disorder, post-traumatic stress disorder, generalized anxiety disorder, anxiety disorder NOS, and organic anxiety disorder.

The term "substance abuse" as used herein means the undesired physical and/or psychological dependence on a drug. The term refers to dependence on a substance such as cocaine, psychedelic agents, marijuana, amphetamines, hallucinogen, phencyclidine, benzodiazepines, alcohol, and nicotine.

The terms "attention deficit hyperactivity disorder" and "ADHD" as used herein mean a condition or disorder characterized by a persistent pattern of inattention, hyperactivity, impulsivity, or any combination thereof.

The term "excessive aggression" as used herein refers to a condition characterized by aggression that is so excessive that it interferes with the individual's daily functions, relationships, and may threaten the safety of the individual, for example in a situation in which violent suicide is contemplated. The excessive aggression which may be treated using the method claimed herein is independent of a psychotic condition and not directly related to the consumption of a drug or other substance.

The term "treating" as used herein includes prophylaxis of the named condition or amelioration or elimination of the condition once it has been established.

Generally, the present inventive subject matter pertains to pharmaceutical compositions comprising a therapeutically effective amount of an antipsychotic agent in combination with a chromium salt; and a pharmaceutically acceptable carrier. In a preferred embodiment, the present inventive subject matter further pertains to pharmaceutical compositions comprising a therapeutically effective amount of olanzapine in synergistic combination with chromium picolinate; and a pharmaceutically acceptable carrier. The amounts of each active agent included within the pharmaceutical compositions of the present invention are selected together to provide a greater than additive effect.

Additionally, the present inventive subject matter relates to methods for augmenting the treatment of psychotic disorders or conditions and/or anxiety disorders by administering to a patient a therapeutically effective amount of a chromium salt in a pharmaceutically acceptable form in conjunction with the administration of a standard antipsychotic agent.

Olanzapine is typically prescribed for the treatment of schizophrenia, as well as other psychotic disorders or conditions and other anxiety disorders. Accordingly, the present inventive subject matter relates to compositions and methods of using chromium picolinate to augment olanzapine's innate ability to treat various psychotic disorders.

The various psychotic disorders which can be augmented in this manner include, but are not limited to, psychosis, acute mania, mild anxiety states, anxiety disorders, schizophrenia, bipolar disorder, autistic disorder, attention deficit hyperactivity disorder ("ADHD"), excessive aggression, substance abuse, tic disorder, and combinations thereof.

In addition to providing this augmented treatment, the present inventive combinations exhibit a lessened liability toward drug-drug interactions than olanzapine alone and a more predictable dosing regimen than olanzapine alone. Additionally, the compositions according to the present inventive subject matter minimize the side effects normally exhibited upon administration of olanzapine alone to a patient, such as weight gain, hyperglycemia, hypertriglyceridemia, hypercholesterolemia, increased adiposity, and negative impact on cognitive function(s). These compositions are also effective for improving dysphoric symptoms.

Other known adverse effects of olanzapine which would be expected to be minimized according to the present inventive subject matter include postural hypotension, constipation, dry mouth, dizziness, fast heart beat, personality disorder, akathisia, tachycardia, irregular pulse, diaphoresis, cardiac dysrhythmia, flu syndrome, nausea, vomiting, hematuria, metrorrhagia, urinary incontinence, abdominal pain, premenstrual syndrome, somnolence, agitation, insomnia, nervousness, headache, dyspnea, tremors, myoglobinuria (rhabdomyolysis), drug-induced Parkinson-ism, amblyopia, and asthenia.

Other antipsychotic agents which are used in the medical arts may also be used in the present invention as a replacement for, or in addition to, olanzapine (i.e., they may be administered in combination with a chromium salt, such as chromium picolinate, to augment their anti-psychotic abilities and to reduce their side effects, such as weight gain). Preferred, non-limiting examples of such additional antipsychotic agents are selected from the group consisting of Acetophenazine Maleate; Alentemol Hydrobromide; Alpertine; Azaperone; Batelapine Maleate; Benperidol; Benzindopyrine Hydrochloride; Brofoxine; Bromperidol; Butaclamol Hydrochloride; Butaperazine; Carphenazine Maleate; Carvotroline Hydrochloride; Chlorpromazine; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Iloperidone; Imidoline Hydrochloride; Lenperone; Loxapine; Mazapertine Succinate; Mesoridazine; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmnitate; Piquindone Hydrochloride; Prochlorperazine Edisylate; Prochlorperazine Maleate; Promazine Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Spiperone; Sulpiride; Thioridazine; Thiothixene; Thorazine; Tioperidone Hydrochloride; Tiospirone Hydrochloride; Trifluoperazine Hydrochloride; Trifluperidol; Triflupromazine; Ziprasidone Hydrochloride; and mixtures thereof. Any of these actives may exhibit a significant weight gain side effect with certain patients, and this side effect can be minimized using the concurrent chromium salt therapy described herein.

In another embodiment of the present inventive subject matter, the pharmaceutical compositions may contain more than one of these antipsychotic agents in combination with the chromium picolinate.

The antipsychotic agents used herein, when used alone or in combination, are administered in therapeutically effective amounts. A therapeutically effective amount will be determined by the parameters discussed below; but, in any event, is that amount which establishes a level of the drug(s) effective for treating a psychotic disorder.

Chromium picolinate is a preferred source of chromium used according to the compositions and methods of the present invention. The synthesis of chromium picolinates is described in U.S. Pat. No. 5,087,623, the entire contents of which are hereby incorporated by reference. A preferred form of the chromium picolinate is chromium tripicolinate. Other acceptable sources of chromium of use according to the present inventive subject matter include without limitation chromium citrate, chromium chloride, chromium nicotinate, chromium polynicotinate, chromium nitrate, chromium oxide, chromium sulfate, chromium phosphate, chromium hydroxide, chromium carbonate, chromium borate, and chromium acetate. Other pharmaceutically acceptable forms of chromium would be apparent to one having ordinary skill in the art.

Since chromium picolinate is shown to optimize insulin levels, and since insulin is known to enhance serotonergic activity by increasing blood-brain barrier transport of tryptophan, chromium picolinate is capable of improving mood in clinical depressives and diabetics receiving the insulin-sensitizing nutrient chromium picolinate.

In addition, the picolinic acid in chromium picolinate can have biochemical, physiological, and behavioral effects of its own on the CNS as analogues of picolinic acid have been shown to impact the metabolism of serotonin, dopamine, and norepinephrine in the brain. Picolinic acid derivatives are known to inhibit dopamine beta hydroxylase thus potentially increasing the dopaminergic tonus of selected areas of the brain. This effect may in turn partially antagonize those adverse effects of antipsychotic agents that stem from excessive D2R dopamine receptor blockade.

When administered, the formulations of the present inventive subject matter are applied in pharmaceutically acceptable compositions. Such preparations may routinely contain salts, buffering agents, preservatives, compatible carriers, and optionally other therapeutic ingredients.

A variety of administration routes are available. The particular mode selected will depend, of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, injectable, intravenous, intramuscular, rectal, sublingual, topical, nasal, transdermal, via implant, trans-mucosal, ocular, buccal, pulmonary, intraperitoneal, intrathecal, or parenteral routes.

The compositions may conveniently be presented in unit dosage form and may be prepared by any of the methods well known in the art of pharmacy.

Preferred, non-limiting examples of oral dosage forms useful according to the present invention include capsules, cachets, tablets, suspensions in aqueous liquors or non-aqueous liquids, a syrup, an elixir, an emulsion, or lozenges, each containing a predetermined amount of the active compound. The oral dosage form may be administered to a patient once, twice, or thrice daily.

Suitable gelling agents which may be useful in the present compositions include aqueous gelling agent, such as neutral, anionic, and cationic polymers, and mixtures thereof. Exemplary polymers which may be useful in the instant compositions include carboxy vinyl polymers, such as carboxypolymethylene. A preferred gelling agent is Carbopol®. Other suitable gelling agents include cellulosic polymers, such as gum arabic, gum tragacanth, locust bean gum, guar gum, xanthan gum, cellulose gum, methylcellulose, hydroxyethylcellulose, hydroxypropylcellulose, and hydroxypropylmethylcellulose.

Other ingredients which may optionally be provided in the instant compositions include humectants, such as propylene glycol; solvents, such as alcohol; and anti-microbial preservatives, such as methylparaben and propylparaben. The topical compositions may also include an organic or inorganic base, such as sodium hydroxide, which is used to adjust the pH of the initial components and the final product.

Carriers such as starches, sugars, and microcrystalline cellulose, diluents, granulating agents, lubricants, binders, disintegrating agents, and the like are suitable in the case of oral solid preparations.

Additionally, the oral dosage forms can be formulated to provide time-release, delayed release, or sustained release of the agents incorporated therein. Such delayed-release systems can avoid repeated administrations of the active compounds of the invention, increasing convenience to the subject and the physician. Many types of release delivery systems are available and known to those of ordinary skill in the art.

Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Other delayed release systems useful according to the present inventive subject matter include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like.

Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

Compositions suitable for rectal administration are described in European Application 0,645,140, the entire disclosure of which is incorporated herein by reference.

Compositions suitable for parenteral administration conveniently comprise a sterile preparation of the conjugates of the invention. This preparation may be formulated according to known methods.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa., the entire contents of which are hereby incorporated by reference.

The present inventive compositions are administered in effective amounts. An effective amount means that amount, alone or with multiple doses, necessary to delay the onset of, inhibit completely or lessen the progression of, or halt altogether the onset or progression of the psychotic disorder while minimizing the incidence of side effects. In general, an effective amount will be that amount necessary to inhibit either negative or positive symptoms of the psychotic condition, preferably both negative and positive symptoms of psychotic disorders.

When administered to a subject, effective amounts will depend on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of the antipsychotic agents will be from about 0.01 mg/kg per day to 1000 mg/kg per day. It is expected that IV doses in the same range will be effective. In the event that the response in a subject is insufficient at such doses, even higher doses (or effective higher doses by a different, more localized delivery route) may be employed to the extent that patient tolerance permits. Continuous IV dosing over, for example, 24 hours or multiple doses per day also are contemplated to achieve appropriate systemic levels of compounds.

The typical total daily dose range for an antipsychotic agent, i.e. olanzapine, for the conditions described herein is from about 1 to 160 mg in single or divided doses. In managing the patient, the therapy should be initiated at a lower dose, perhaps at about 1 mg antipsychotic agent and increased to a desired dose depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art.

Generally, daily oral doses of the chromium salt will be from about 50 to about 5,000 μg daily. A more preferred range is about 100 to about 1,500 μg chromium salt daily, with about 200 to about 1,000 μg chromium salt daily especially preferred in this regard. The preferred form of chromium salt is chromium picolinate.

Stated differently, a preferred range is about 0.7 μg to about 70 μg chromium salt per kilogram body weight of the patient daily. A more preferred range is about 1.5 μg to about 21.5 μg chromium salt per kilogram body weight of the patient daily.

A most preferred range is about 2.5 μg to about 14.5 μg chromium salt per kilogram body weight of the patient daily. This dosage range is generally several fold greater than that contained in most commercially available multi-vitamin and mineral preparations.

It is also preferable to take the last, or only, daily dose of chromium eight (8) hours prior to sleep to avoid insomnia. In a preferred embodiment, the daily dose of chromium is taken at least four (4) hours prior to sleep. In a particularly preferred embodiment, the daily dose of chromium is taken at least (2) hours prior to sleep. In a most preferred embodiment, the daily dose of chromium is taken at least one (1) hour prior to sleep. It is also noted that diabetics and hypoglycemics should use chromium salts only under a physician's supervision.

In practicing the methods of treatment of the present invention, chromium picolinate (or another pharmaceutically-acceptable salt of chromium) is administered to a patient concurrently with olanzapine as a part of olanzapine therapy (or therapy with another of the antipsychotic actives described above). The olanzapine or other antipsychotic actives will be administered using their conventional routes of administration and their conventional dosage levels. Chromium picolinate may be administered to the patient in any way known in the art, although oral administration will generally be most convenient.

A tablet or capsule for oral administration of the present invention would typically include from about 1 mg to about 40 mg of olanzapine, and from about 100 μg to about 1500 μg of chromium picolinate. Conventional formulational aides, such as fillers, coatings, preservatives, disintegrants, colorings and flavoring agents, can also be included at their conventional art-established levels. When the composition contains other actives, in place of olanzapine, their levels per dosage typically would be in accordance with the typical levels for each of the actives known in the art.

The invention is further defined by reference to the following examples describing in detail the preparation of the compositions of the present invention, as well as their utility. It will be apparent to those skilled in the art that many modifications, both to materials and methods, may be practiced without departing from the invention.

The following compositions can be used to prepare oral dosage forms according to the presently claimed invention:

EXAMPLE 1

The following is a typical formula used as a specific representative of the oral dosage forms which may be provided according to the presently claimed invention.

TABLE I

| Ingredient | Quantity (mg/capsule) |
|---|---|
| Olanzapine | 5 mg |
| Chromium picolinate | 1000 μg |
| Starch, dried | 170 |
| Magnesium stearate | 10 |

The components of Example 1 can be blended together and compressed to form tablets.

EXAMPLE 2

The following is a typical formula used as a specific representative of the oral dosage forms which may be provided according to the presently claimed invention.

TABLE II

| Ingredient | Quantity (mg/tablet) |
| --- | --- |
| Olanzapine | 10 mg |
| Chromium picolinate | 1000 µg |
| Cellulose, microcrystalline | 285 |
| Silicon dioxide, fumed | 10 |
| Stearic Acid | 5 |

The components of Example 2 can be blended together and compressed to form tablets.

EXAMPLE 3

TABLE III

| Ingredient | Quantity (mg/tablet) |
| --- | --- |
| Olanzapine | 15 mg |
| Chromium picolinate | 1000 µg |
| Starch | 50 |
| Microcrystalline cellulose | 45 |
| Polyvinylpyrrolidone | 4 |
| Sodium carboxymethyl starch | 4.5 |
| Magensium stearate | 0.5 |
| Talc | 1 |

The active ingredients, starch and cellulose may be passed through a No. 45 mesh U.S. sieve and mixed thoroughly. The aqueous solution containing polyvinyl-pyrrolidone may be mixed with the resultant powder, and the mixture then may be passed through a No. 14 mesh U.S. sieve. The granules so produced may be dried at 50° C. and passed through a No. 18 mesh U.S. Sieve. The sodium carboxymethyl starch, magnesium stearate and talc, previously passed through a No. 60 mesh U.S. sieve, may then be added to the granules which, after mixing, may be compressed on a tablet machine to yield tablets.

EXAMPLE 4

TABLE IV

| Ingredient | Quantity (mg/capsule) |
| --- | --- |
| Olanzapine | 20 mg |
| Chromium picolinate | 1000 µg |
| Starch | 64 |
| Microcrystalline cellulose | 64 |
| Magnesium stearate | 2 |

The active ingredient, cellulose, starch, and magnesium stearate may be blended, passed through a No. 45 mesh U.S. sieve, and filled into hard gelatin capsules.

EXAMPLE 5

TABLE V

| Ingredient | Quantity (mg/capsule) |
| --- | --- |
| Olanzapine | 40 mg |
| Chromium picolinate | 1000 µg |
| Starch | 54 |
| Microcrystalline cellulose | 54 |
| Magensium stearate | 2 |

The components of Example 5 can be blended together and compressed to form tablets.

EXAMPLE 6

A patient is suffering from side effects resulting from antipsychotic agent therapy. An oral dosage form in accordance with any of Examples 1 through 5 is administered. It would be expected that the patient would improve his/her condition and the incidence of said side effects would be reduced.

EXAMPLE 7

A patient is suffering from weight gain resulting from antipsychotic therapy. An oral dosage form in accordance with any of Examples 1 through 5 is administered. It would be expected that the patient would improve his/her condition and the weight gain would be reduced.

EXAMPLE 8

A patient is suffering from hyperglycemia resulting from antipsychotic therapy. An oral dosage form in accordance with any of Examples 1 through 5 is administered. It would be expected that the patient would improve his/her condition and the hyperglycemia would be reduced.

EXAMPLE 9

A patient is suffering from a psychotic disorder. An oral dosage form in accordance with any of Examples 1 through 5 is administered. It would be expected that the patient would improve his/her condition.

The invention being thus described, it will be obvious that the same may be varied in many ways. Such variations are not to be regarded as a departure from the spirit and scope of the invention and all such modifications are intended to be included within the scope of the following claims.

I claim:

1. A pharmaceutical composition comprising;
   a therapeutically effective amount of an antipsychotic agent in combination with about 100 µg to about 1500 µg of a chromium salt; and
   a pharmaceutically acceptable carrier.

2. The pharmaceutical composition of claim 1, wherein said chromium salt is chromium picolinate.

3. The pharmaceutical composition of claim 1, wherein said antipsychotic agent is olanzapine.

4. The pharmaceutical composition of claim 1, formulated for oral administration.

5. The pharmaceutical composition of claim 1, which contains about 1 mg to about 160 mg of the antipsychotic agent.

6. The pharmaceutical composition of claim 5, which contains about 1 mg to about 40 mg of the antipsychotic agent.

7. The pharmaceutical composition of claim 1, which contains about 200 µg to about 1000 µg of the chromium salt.

8. A method for minimizing side effects in a patient taking an antipsychotic agent, comprising administering a therapeutically effective amount of said antipsychotic agent in combination with about 100 μg to about 1500 μg of a chromium salt to said patient, wherein said side effects are caused by taking said antipsychotic agent and are selected from the group consisting of weight gain, hyperglycemia, hypertriglyceridemia, hypercholesterolemia, increased adiposity, negative impact on cognitive function(s), and combinations thereof.

9. The method of claim 8, wherein said chromium salt is chromium picolinate.

10. The method of claim 8, wherein said antipsychotic agent is olanzapine.

11. The method of claim 8, comprising administering about 1 mg to about 160 mg of the antipsychotic agent.

12. The method of claim 11, comprising administering about 1 mg to about 40 mg of the antipsychotic agent.

13. The method of claim 8, comprising administering about 200 μg to about 1000 μg of the chromium salt.

14. A method for reducing weight gain in a patient taking an antipsychotic agent, comprising administering a therapeutically effective amount of said antipsychotic agent in combination with about 100 μg to about 1500 μg of chromium picolinate to said patient, wherein said weight gain is caused by taking said antipsychotic agent.

15. The method of claim 14, wherein said antipsychotic agent is olanzapine.

16. A method for reducing incidence of hyperglycemia in a patient taking an antipsychotic agent, comprising administering a therapeutically effective amount of said antipsychotic agent in combination with about 100 μg to about 1500 μg of chromium picolinate to said patient, wherein said hyperglycemia is caused by taking said antipsychotic agent.

17. The method of claim 16, wherein said antipsychotic agent is olanzapine.

* * * * *